United States Patent [19]

Mueller

[11] Patent Number: 4,986,757

[45] Date of Patent: Jan. 22, 1991

[54] NUTRITION AND EXERCISE EDUCATION GAME AND METHOD OF PLAY THEREOF

[76] Inventor: Laverne J. Mueller, 5491 Crathes Ct., St. Louis, Mo. 63119

[21] Appl. No.: 404,588

[22] Filed: Sep. 8, 1989

[51] Int. Cl.⁵ .............................................. G09B 19/00
[52] U.S. Cl. .................................... 434/127; 434/128; 434/129; 273/242; 273/275; 273/287
[58] Field of Search ........................ 434/127, 128, 129; 273/236, 242, 243, 275, 287, 288, 302

[56] References Cited

U.S. PATENT DOCUMENTS

| | | |
|---|---|---|
| 1,631,505 | 6/1927 | Samis . |
| 4,159,117 | 6/1979 | Kuna ..................................... 273/243 |
| 4,216,966 | 8/1980 | MacRae ............................... 273/243 |
| 4,230,320 | 10/1980 | Crew, Jr. ............................. 273/243 |
| 4,440,396 | 4/1984 | Frudakis ........................... 434/127 X |

Primary Examiner—Richard J. Apley
Assistant Examiner—Jennifer L. Doyle
Attorney, Agent, or Firm—Edward R. Weber

[57] ABSTRACT

A board game aimed at three to six year olds which is designed to teach and promote good nutrition and exercise habits which result in healthy cardiovascular systems to young children as well as provide entertainment and reinforcement for normative values.

8 Claims, 3 Drawing Sheets

NUTRITION AND EXERCISE EDUCATION GAME AND METHOD OF PLAY THEREOF

FIELD OF THE INVENTION

This invention relates to games, and more particularly, to instructional games designed to teach and promote good nutrition and exercise habits in young children as well as provide entertainment and reinforcement of normative values.

BACKGROUND OF THE INVENTION

A growing number of Americans, as well as scientists and health professionals, are becoming increasingly aware of the interrelatedness of good nutrition and exercise habits and a healthy cardiovascular system. Similarly, there is a growing awareness that it is easier to instill good habits at an early age rather than to effect a change in poor habits at a later age. As a result a number of nutrition-oriented games have been developed which attempt to provide educational features which impart information to allow informed choices regarding calories, sodium intake, saturated and polyunsaturated fats, cholesterol, and the like. Among the games developed are U.S. Pat. No. 4,040,628 (Pope), a diet game which concerns itself with weight loss, U.S. Pat. No. 4,174,840 (Curtiss), a game which emphasizes the relationship between food consumption, exercise, and weight control, and U.S. Pat. No. 4,398,721 (McKay), a game which concerns itself with a nutritional characteristic and daily requirements for good health.

All of the aforementioned games are directed to older individuals and attempt to modify established behavior through instruction. The game of the present invention is directed toward three to six year olds and attempts to teach good nutrition and exercise habits in the formative years thereby ensuring that individuals will recognize and practice informed choices throughout their lives.

Accordingly it is the general object of the present invention to provide a game apparatus from which habits conducive to good cardiovascular health will result. It is another object of the present invention to provide a game which affords entertainment while imparting the nutritional skills necessary to make informed choices and recognition of the role of exercise in good health. It is a further object of the present invention to reinforce normative values. Other objects and features will be in part apparent and in part pointed out hereinafter.

SUMMARY OF THE INVENTION

The present invention is a game board apparatus for a nutrition education game aimed at three to six year olds which is designed to be played by two or more players. While it is not necessary that one of the players be an adult, it is generally advisable since one of the players will need to be able to read the information presented on the game cards.

The game apparatus includes a game board on which a heart-shaped playing path consisting of contiguous, sequential spaces is imprinted; a chance determining means, such as a spinner or die and cup; a plurality of game cards on which a positive or negative statement is imprinted together with instructions for how to proceed; a plurality of heart-shaped game tokens on which is imprinted a stylized happy or sad face; and a plurality of playing pieces.

To play the game, each player chooses a playing piece which he places on the "Start" space. A first player is then chosen by some agreed upon manner, such as whomever gets the highest number on a turn of the spinner, and play then proceeds in a clockwise fashion. The first player then spins and traverses the playing path the number of spaces indicated by the spinner. He then draws a game card which contains either a positive or negative statement and follows the instructions contained on the game card respecting taking a "happy face" heart-shaped game token or a "sad face" heart-shaped game token. The player to the left of the first player then spins, moves his playing piece the indicated number of spaces on the playing path, selects a game card, and then acts accordingly. Play continues in this fashion until all players have traversed the entire playing path. At that time, each player matches and discards one "happy face" heart-shaped game token for each "sad face" heart-shaped game token he holds. The winner is the player who has the most "happy face" heart-shaped game tokens remaining.

As the game is played, each player's playing piece will land on a plurality of sequential spaces on which are imprinted foods and exercises which are necessary to good cardiovascular health. The foods shown are selected from the four basic food groups. The exercises shown are activities which require the heart to sustain a certain level of activity for an extended period of time. Through association, then, a child will learn what types of foods and activities are needed to keep his heart healthy.

In a preferred embodiment, all the component game parts are created and decorated to reinforce certain physiological facts, the positive value of good nutrition and exercise on the cardiovascular system, and the positive value of conducting oneself in accordance with normative values. For instance, on the game board, the contiguous playing path is a conventional stylized heart shape and the background is decorated with happy children some of whom are playing ball, others of whom are playing on playground equipment, and still others of whom are playing with their pets. A background showing exercise was chosen to reinforce the fact that the heart is a muscle which requires regular exercise. Further, the playing path itself shows the types of foods and exercise requisite for good health. Likewise, the indicia on the spinner is attractively colored fresh fruits and vegetables. The playing cards are a rich red to associate one's behavior with the heart. Additionally, when the behavior indicated on the card is positive, the player chooses a red, heart-shaped token with a smile on it. When the behavior described is negative, the player chooses a red, heart-shaped token with a frown on it. Finally, the playing pieces are shaped like children.

DETAILED DESCRIPTION OF THE DRAWINGS

Figure 1:
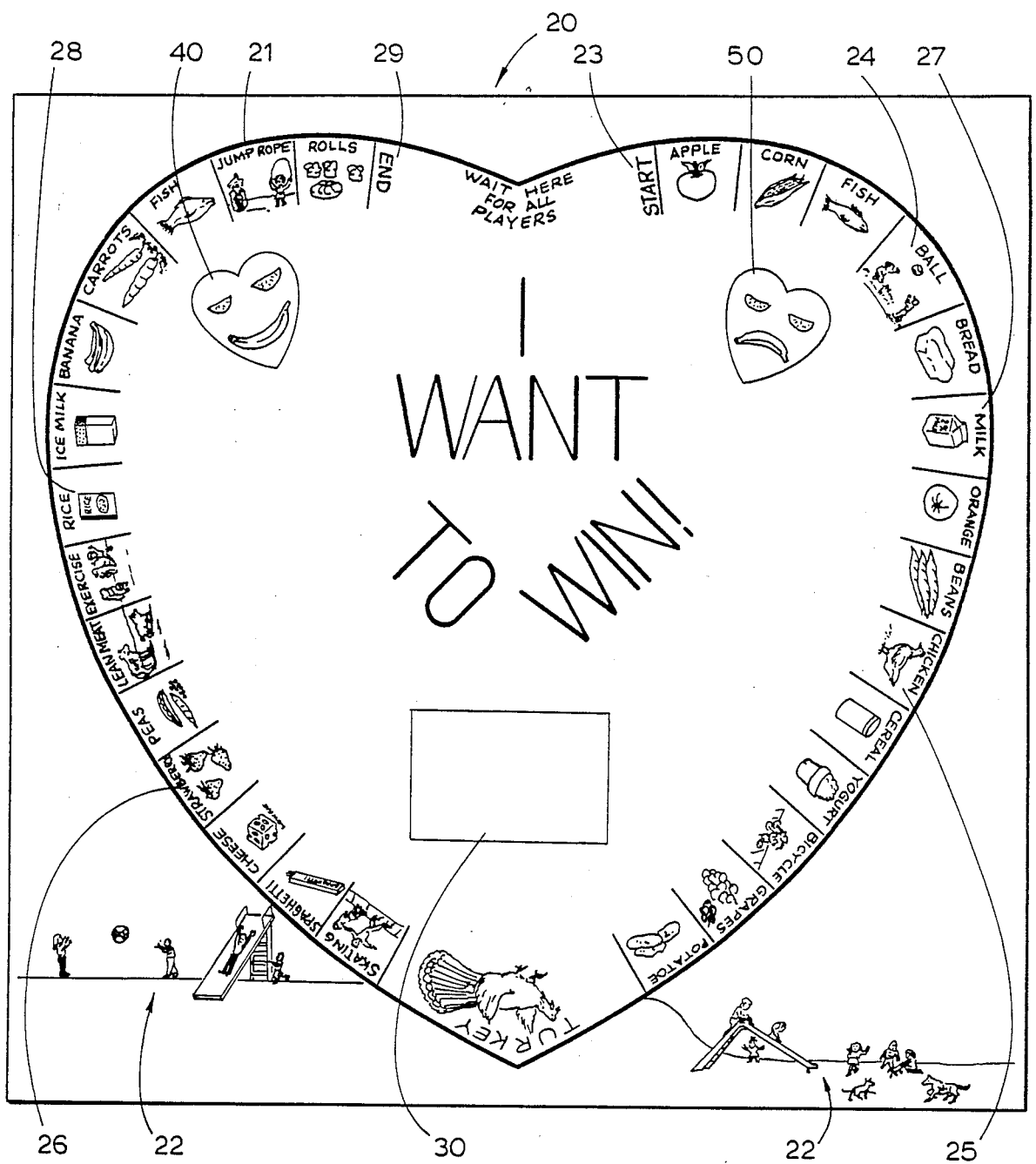
FIG. 1 is a plan view of the playing board of the present invention.

Referring now to the drawings wherein like reference characters represent like elements, FIG. 1 shows a game board 20, which is of a conventional square shape, on which is imprinted a heart-shaped playing path 21. The background of game board 20 is further imprinted with indicia 22 depicting exercise in which three to six year old children might engage. The area within playing path 21 is imprinted with a "happy face" heart shape 40, a "sad face" heart shape 50, and a designated area 30 for the game cards.

Playing path 21 is formed from thirty contiguous, sequential spaces on which foods from each of the four basic food groups and exercise conducive to good cardiovascular health are depicted. The four basic food groups include: (1) cereal, breads and other grains, (2) lean meat and low-fat cheese, (3) lowfat milk and dairy products, and (4) fruits and vegetables. Pointed out in particular on playing path 21 are a start space 23, an exercise space 24 denoted as "ball", lean meat and lowfat cheese spaces, such as space 25 labeled "chicken", fresh fruit and vegetable spaces, such as space 26 labeled "strawberry", lowfat milk and dairy spaces, such as space 27 labeled "milk", cereal, bread and other grains spaces, such as space 28 labeled "rice", and an end space 29. Also shown is "happy face" heart shape 40, which corresponds to a "happy face" heart-shaped game tokens 41 (FIG. 4), "sad face" heart shape 50, which corresponds to a "sad face" heart-shaped game tokens 51 (FIG. 5), and designated area 30 for game cards 31 (FIG. 2) and game cards 32 (FIG. 3). Close examination of playing path 21 will reveal the following spaces, which are randomly intermixed along the playing path:

| Cereal, Breads, and Other Grains Group | Lean Meat and Lowfat Cheese |
|---|---|
| Bread | Cheese |
| Cereal | Chicken |
| Rice | Fish (2) |
| Rolls | Lean Meat |
| Spaghetti | Turkey |
| Lowfat Milk and Dairy Products | Fruits and Vegetables |
| Ice Milk | Apple |
| Milk | Banana |
| Yogurt | Beans |
| Exercise | Carrots |
| Bicycle | Corn |
| Ball | Grapes |
| Exercise | Orange |
| Jump Rope | Peas |
| Skating | Potato |
|  | Strawberry |

Figure 2:
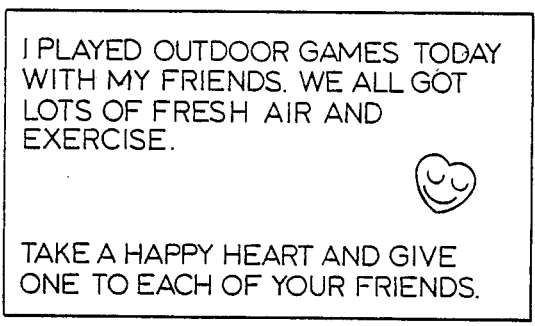
FIG. 2 depicts one of the plurality of game cards which impart positive information together with instructions for the game players.
Figure 3:
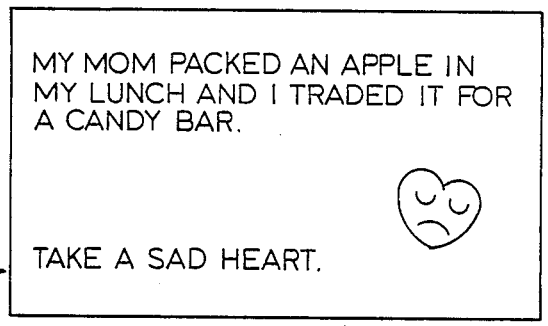
FIG. 3 depicts one of the plurality of game cards which impart negative information together with instructions for game players.

FIG. 2 shows a game card in greater detail. These game cards contain a positive statement and instructions to take a "happy face" heart-shaped game token 41, shown at FIG. 4. In a preferred embodiment the cards are red with white writing to reinforce the concept of a healthy heart.

Other positive statements shown on the cards include:

I had oatmeal for breakfast instead of sugar flakes.

I had ice milk instead of ice cream because it doesn't have so much fat in it.

I had raisins instead of a candy bar and I brushed my teeth after I was finished eating them.

I had popcorn for a snack and it was flavored with margarine instead of butter and I went easy on the salt.

I had a peanut butter sandwich instead of a hamburger for lunch. I couldn't brush my teeth when I finished but I rinsed my mouth with some water. It's good but it really does stick to my teeth.

I had juice, cereal, and light wheat toast for breakfast. And, I had a glass of lowfat milk. I know breakfast is an important meal.

I had pretzels instead of potato chips. Pretzels are a better choice because they are not so greasy.

Today I had a big bunch of grapes for a snack after school.

I had a banana for a snack today.

I was riding my bike and I got home before dark like I'm supposed to. I know that is the safe thing to do.

I went to the grocery store with my mom and dad. The cart was filled with healthy foods and I did not bug them for junk food.

I went to visit my grandparents today and I took them some fruit.

I helped my mom and dad rake the leaves and clean up the yard. I had a good time and got lots of exercise.

We have a new classmate at school and I invited him to play at recess with me and my friends.

One of my classmates was having a hard time with some school work. I know how to do it, so I helped. It makes me feel good inside when I help people.

FIG. 3 shows a game card 32 in greater detail. These game cards contain a negative statement and instructions to take a "sad face" heart-shaped game token 51, shown at FIG. 5. In a preferred embodiment the cards are red with white writing to reinforce the concept of a healthy heart.

Other negative statements shown on the cards include:

I saved my milk money to buy candy after school.

My mom packed an apple in my lunch and I traded it for a candy bar.

The box of cereal I picked at the store is sugar coated. I know the healthy cereal does not have any added sugar.

My choice for a snack was a bag of chips and a soda.

I skipped breakfast. I know that's no way to start the day.

My after school snack was soda and cookies and I didn't even brush my teeth after eating all that sweet stuff.

I put too much salt on my food.

I was playing outside and I came in to get a drink. My choice was a soda.

My mom and dad wanted to take a walk with me tonight but I wanted to play video games. A walk would have been good exercise.

I was riding my bike and I did not get home before dark like I was supposed to. I know it is not safe to ride after it gets dark.

My friends came by for me to play outdoors but I stayed in and watched cartoons on TV.

I was talking and disturbing the rest of my classmates at school today.

Figure 4:
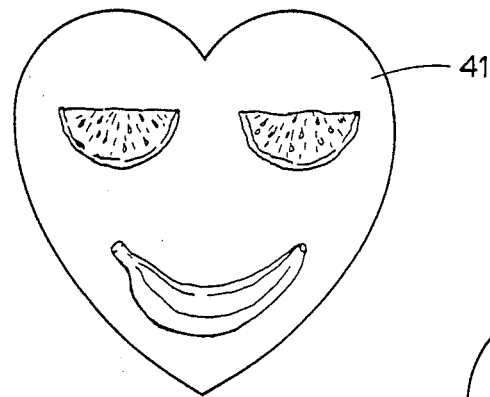
FIG. 4 is a plan view of a "happy face" game token.

FIG. 4 shows a "happy face" heart-shaped game token 41 which is seen to have "eyes" made from an orange section and a "mouth" from a banana. In a preferred embodiment, the game token is red with the eyes being orange and the mouth being yellow.

Figure 5:
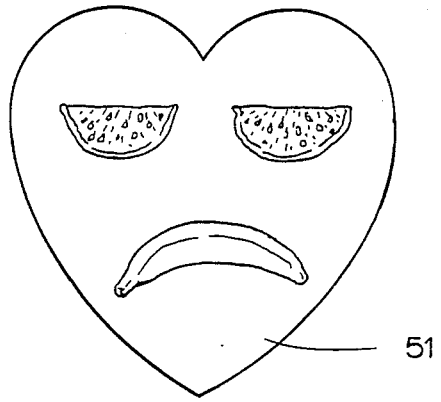
FIG. 5 is a plan view of a "sad face" game token.

FIG. 5 shows a "sad face" heart-shaped game token 51 which is likewise seen to have "eyes" made from an orange section and a "mouth" from a banana. Once again, in a preferred embodiment, the game token is red with the eyes being orange and the mouth being yellow.

Figure 6:
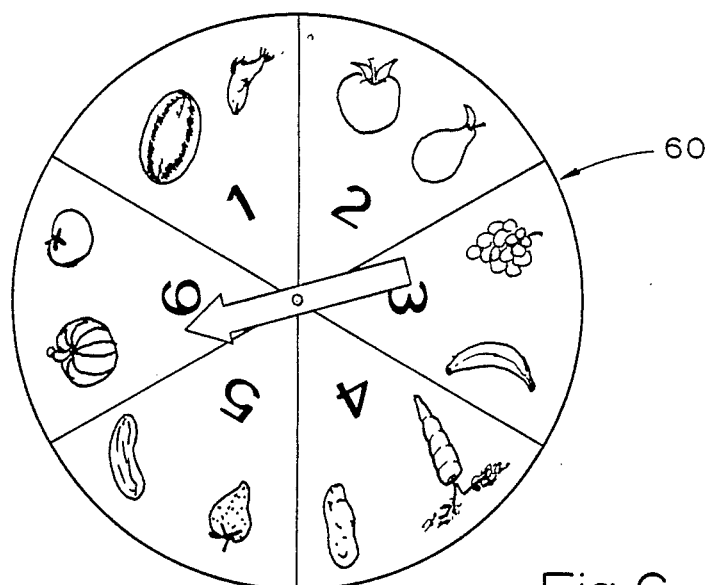
FIG. 6 is a plan view of the spinner of the present invention.

FIG. 6 illustrates a spinner 60 bearing the numbers 1 through 6. The spinner is decorated with various food items including a watermelon, fish, apple, pear, grapes, banana, carrot, potato, strawberry, pickle, pumpkin, and tomato as might be seen in a preferred embodiment.

Figure 7:
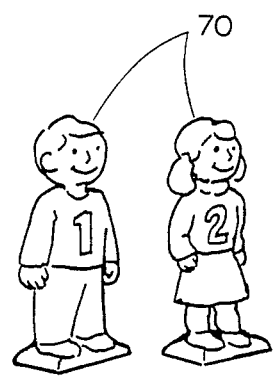
FIG. 7 depicts playing pieces constructed in accordance with a preferred embodiment of the present invention.

FIG. 7 shows the playing pieces 70 which are stylized children who are smiling, active, and healthy.

The procedures and rules of the game with respect to the illustrated embodiment are rather simple. A first player is chosen by some agreed upon manner, such as whoever receives the highest number from a spin of spinner 60. That player then spins spinner 60 and moves his playing piece along the playing path the number of spaces indicated. He then picks the top card 31/32 from the stack of game cards located in designated area 30, reads the statement to all the players (or has the statement read to all the players), and selects a "happy face" heart-shaped game token 41 or "sad face" heart-shaped game token 51 as directed by the game card. He then returns the selected game card to the bottom of the stack of game cards thereby ending his turn. Play then moves in a clockwise fashion and continues until all players have successfully traversed the playing path. Each player then matches one of his "happy face" heart-shaped game tokens 41 with one of his "sad face" heart-shaped game tokens 51 and discards the pair of tokens. Whoever has the most "happy face" heart-shaped game tokens remaining is declared the winner.

As will be understood, players participating in this game will quickly learn what types of foods and exercise are requisite to good cardiovascular health. Additionally, they will receive reinforcement of formative nutritional and behavioral values. Because the nutritional information and behavioral values are learned via an enjoyable and attractive game, the information is quickly absorbed and retained. Further, because the information and values are learned at an early age, their use will more be likely to be practiced throughout the players' lives.

It should be noted that the foregoing drawings and accompanying descriptions are intended to be exemplary of a preferred embodiment of the invention and are not intended to be exhaustive of the possibilities of the games or types of games within the intended scope of the invention. It should also be understood that modifications will readily occur to those skilled in the art within the spirit of the invention. Such modifications could include changing the chance determining means to a cup and die, adding other positive and negative statements to the game cards, and including blank game cards on which the players could write their own statements. The game cards could also contain short questions with a correct answer being rewarded with a "happy face" heart-shaped game token and an incorrect answer being rewarded with a "sad face" heart-shaped game token. The present invention could be also modified to appeal to various other age groups, including adults.

In view of the above, it will be seen that the several objects of the invention are achieved and that other advantageous results are attained. As various changes could be made in the above product without departing from the scope of the invention, it is intended that all matter contained in the above description or shown in the accompanying drawing shall interpreted as illustrative and not in a limiting sense.

What is claimed is:

1. A method of teaching good health habits and normative values to three to six year old children utilizing a board game which presents information to the children that reinforces nutritional and exercise habits capable of producing a healthy cardiovascular system, wherein each player selects a playing piece to represent said player and in turn operates a chance determining means to select a first player; said first player, and each player in turn, then operates said chance determining means and moves said playing piece in discrete steps along a playing path in accordance with the respective integer selected by said chance determining means, wherein said path consists of a start space, a plurality of intermixed food spaces and exercise spaces, and an end space and wherein said food spaces include foods from each of the basic four food groups and wherein said exercise spaces include activities which promote physical fitness resulting in good health, draws one game card from a deck of game cards after said player's playing piece comes to rest after transversing the aforementioned discrete steps, reads said game card which contains a statement which imparts information relating to parameters affecting individual health together with directions for the next action to be taken by said player, follows the directions given to said player by said game card, returns said game card to the bottom of the deck, and draws a positive game token or a negative game token in accordance with said directions form a container holding a plurality of said game tokens, and wherein after each player has successfully transversed the entire playing path, each player matches said game tokens drawn by said player so that one positive game token is matched with one negative game token, discards each matched set of game tokens, and tallies any remaining positive game tokens, and wherein the respective totals of positive game tokens retained by each player are then compared to select as the winner the player having the greatest remaining total of positive game tokens.

2. A method of teaching habits capable of producing good health and normative values according to claim 1 wherein said chance determining means is a spinner having a plurality of integers randomly distributed around the periphery.

3. A method of teaching habits capable of producing good health and normative values according to claim 1 wherein said chance determining means of said game is a cup and die.

4. A method of teaching habits capable of producing good health and normative values according to claim 1 wherein a plurality of game cards are blank to allow game players to include their own statements relating to nutrition, exercise, and normative values.

5. A method of teaching habits capable of producing good health and normative values according to claim 1 wherein the positive game tokens are marked with happy faces and the negative game tokens are marked with said faces.

6. A method of teaching habits capable of producing good health and normative values according to claim 1 wherein a plurality of said game cards contain statements which provide nutrition information which either positively or negatively affects health.

7. A method of teaching habits capable of producing good health and normative values according to claim 1 wherein a plurality of said game cards contain statements which provide exercise information which either positively or negatively affects health.

8. A method of teaching habits capable of producing good health and normative values according to claim 1 wherein a plurality of said game cards contain statements which impart information pertaining to normative values.

* * * * *